United States Patent [19]

Hughes et al.

[11] 4,431,546

[45] Feb. 14, 1984

[54] AFFINITY CHROMATOGRAPHY USING METAL IONS

[75] Inventors: Peter Hughes, Salisbury; Christopher R. Lowe, Eastleigh; Roger F. Sherwood, Salisbury, all of England

[73] Assignee: The Public Health Laboratory Services Board, London, England

[21] Appl. No.: 372,021

[22] Filed: Apr. 26, 1982

[30] Foreign Application Priority Data

Apr. 27, 1981 [GB] United Kingdom ............... 8112925

[51] Int. Cl.³ .................................... B01D 15/08
[52] U.S. Cl. ............................. 210/656; 210/198.2; 210/502.1
[58] Field of Search .............. 210/635, 656, 198.2, 210/502; 435/815

[56] References Cited

U.S. PATENT DOCUMENTS 4,016,149  4/1977  Travis et al. ............... 210/635 X
4,118,316  10/1974  Talley et al. ............... 210/635
4,336,161  6/1982  Rosevear et al. ........... 210/635 X

FOREIGN PATENT DOCUMENTS

WO79/00541  8/1979  PCT Int'l Appl.

OTHER PUBLICATIONS

Chromatographic and Allied Methods by Mikes, John Wiley & Sons, New York,, pp. 388–391 and 407–410, 1979.

Methods in Enzymology by Lorand, (vol. XLV), Academic Press, New York, pp. 462–466, 1976.

Primary Examiner—John Adee
Attorney, Agent, or Firm—Cushman, Darby & Cushman

[57] ABSTRACT

A process for the affinity chromatographic separation of at least one biological or related substance from a mixture wherein the at least one biological or related substance is bound to a binding material, having a ligand containing at least one of the groups anthraquinone, phthalocyanine or aromatic azo, in the presence of at least one metal ion selected from the group $Ca^{2+}$, $Sr^{2+}$, $Ba^{2+}$, $Al^{3+}$, $Co^{2+}$, $Ni^{2+}$, $Cu^{2+}$ or $Zn^{2+}$. The preferred metal ions are $Co^{2+}$, $Ni^{2+}$ and $Zn^{2+}$, with $Zn^{2+}$ being particularly preferred. The ligand may be linked directly to the matrix or via a spacer arm. The process may be performed at atmospheric pressure or under pressure, especially high pressure (100–3500 psi). The nature of the contact, washing and eluting solutions depends on the substance to be separated. Generally the contact solution is made up of the substance to be separated and a metal salt dissolved in a buffer solution, while the washing solution comprises the same metal salt dissolved in the same buffer. The eluting solution, may be a buffer solution, either alone or containing a chelating agent or it may be an alkali metal salt or a specific desorbing agent. Alternatively the eluting solution may be a mixture of two or more of these solutions or two or more of these solutions used consecutively.

32 Claims, 1 Drawing Figure

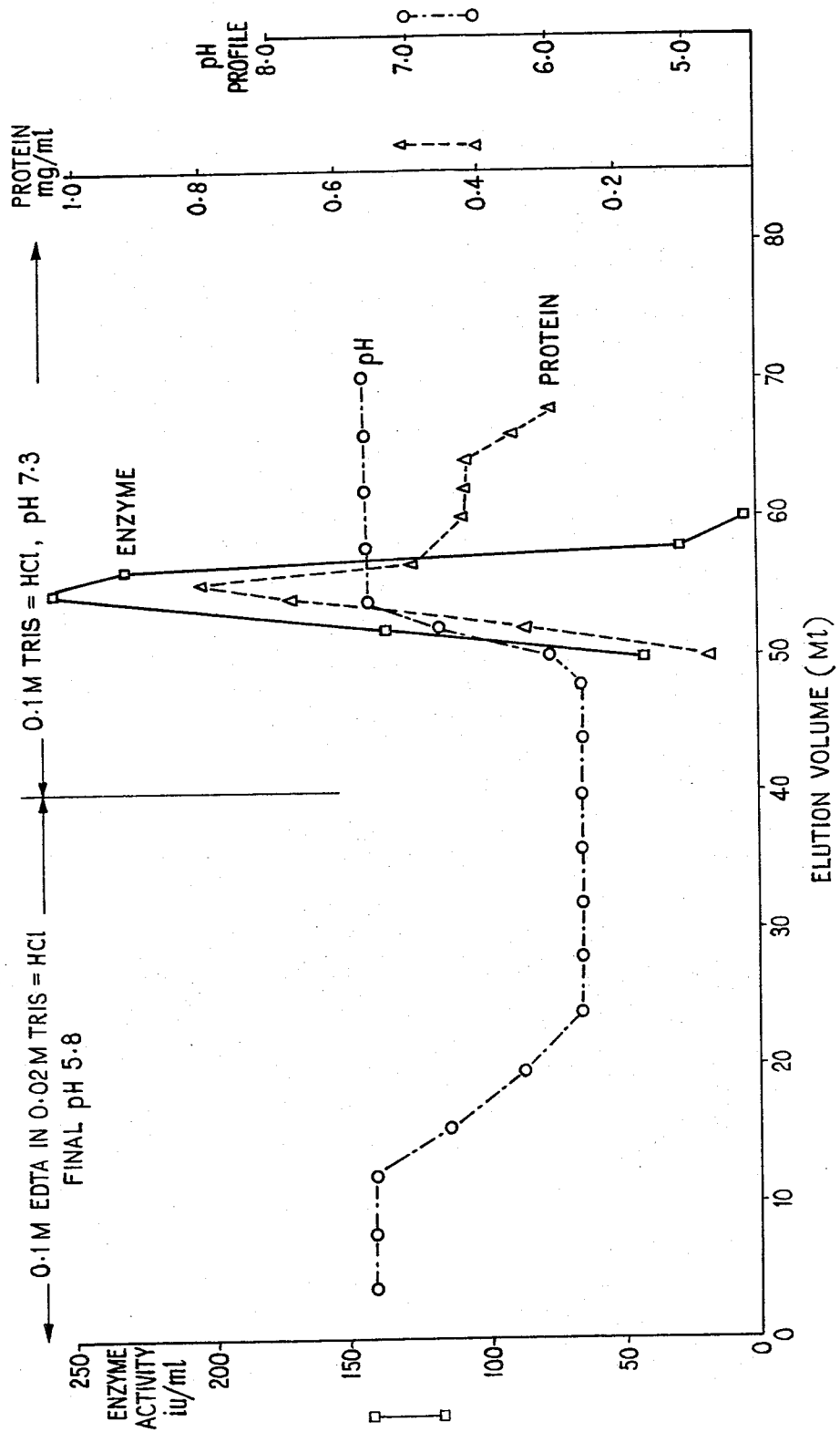

AFFINITY CHROMATOGRAPHY USING METAL IONS

The present invention relates to a process for the affinity chromatographic separation of biological or related substances from a mixture and to biological or related substances when separated by said process.

Affinity chromatography is a well known technique for the separation of biological or related molecules which employs the biospecific interactions between the molecule being isolated and another molecule (ligand) immobilised on a stationary support (matrix). The ligand must interact specifically and reversibly with the molecule to be separated. It is generally immobilised on the support by reacting a ligand precursor with the matrix.

A typical affinity chromatographic process comprises, (a) The contact phase, wherein a contact solution comprising a mixture containing the desired biological or related substance is contacted with a binding material so that the desired substance binds to the binding material. Generally, the binding material is composed of a ligand attached to a matrix.

(b) The washing phase, wherein the non-binding species are removed from the binding material by passing a washing solution therethrough, and (c) The elution phase, wherein an eluting solution is passed through the binding material to recover the desired biological or related substance.

Chromatographic systems wherein the ligands are derivatives of reactive dyes, particularly derivatives of anthraquinones, phthalocyanines or aromatic azo compounds, especially diazinyl or triazinyl derivatives thereof, and are bound to suitable matrices, especially polyamino or polyhydroxylic matrices have been used with great success in the affinity chromatography art. It is important in these, as in other, systems that a high percentage of the desired biological or related substance should bind to the binding material during the contact phase. It is an aim of the present invention to improve the percentage binding of biological or related substances to binding materials having ligands of the reactive dye type.

According to the present invention there is provided a process for the affinity chromatographic separation of at least one biological or related substance from a mixture wherein the at least one biological or related substance is bound to a binding material, having a ligand containing at least one of the groups anthraquinone, phthalocyanine or aromatic azo, in the presence of at least one metal ion selected from the group $Ca^{2+}$, $Sr^{2+}$, $Ba^{2+}$, $Al^{3+}$, $Co^{2+}$, $Ni^{2+}$, $Cu^{2+}$ or $Zn^{2+}$.

The choice of metal ion in a separation process according to this invention will be determined by the structure of both the biological or related substance and the binding material. Not all of the listed metal ions will improve the binding of all biological or related substances to all ligands, however the present invention does provide a process in which, in all cases, at least one of the metal ions improves binding and in which, in many cases, at least three of the metal ions improves binding.

Of the metal ions listed it has been found that $Co^{2+}$, $Ni^{2+}$ and $Zn^{2+}$ improve the binding of the widest range of substances, with $Zn^{2+}$ being the best of all.

It should be noted that although 100% (by activity) binding of biological or related substance to binding material (in the contact phase) is preferred, it is evident that a percentage binding below that level will often be a significant improvement over an analogous affinity chromatographic process performed in the absence of a metal ion. It is the present inventors experience that even a 30% binding level may be useful, although a level of at least 70% is generally preferred.

The biological or related substance may be any material that binds specifically to the ligands employed in the process of the present invention, for example, peptides, polypeptides, proteins, nucleotides, polynucleotides, nucleic acids, steroids, lipids or hormones. Generally however the biological or related substance will be an enzyme, protein or polypeptide, for example albumin such as ovalbumin, kinases such as hexokinase, glycerokinase or urokinase, carboxypeptidases, alkaline phosphatases, nucleases such as restriction endonucleases, dehydrogenases such as glyceraldehyde - 3 -phosphate dehydrogenase, esterases, DNA or RNA binding proteins.

The ligand is any material containing an anthraquinone, preferably a sulphonated anthraquinone, phthalocyanine or aromatic azo group which interacts with the biological or related substance to be separated both specifically and reversibly. The ligands of the present invention preferably are derived from ligand precursors commonly known as reactive dyes. These dyes include pyrazinyl, pyrimidinyl, pyridazinyl or sulphone derivatives of an anthraquinone (I) or an aromatic azo group (II),

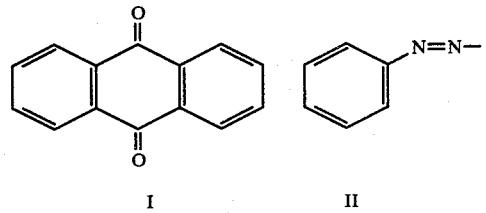

For example, dyes sold under the trade marks Reactone (J R Geigy SA), Drimarene (Sandoz Ltd), Levafix (Farbenfabriken Bayer AG), Cavalite (Du Pont de Nemours Inc), Remazol (Farbwerke Hoechst AG) and Primazin (Badische Anilin u Soda Fabrik AG).

Preferably however the dyes are triazinyl derivatives of anthraquinones, phthalocyanines or aromatic azo compounds. Such compounds have the general formula III

wherein A is an organic substituent containing an anthraquinone, preferably a sulphonated anthrquinone, an aromatic azo or a phthalocyanine group; B is an organic substituent, preferably a sulphonated aromatic group, a halogen atom, preferably a chlorine atom, or an amino or substituted amino group; and C is a leaving group, preferably a chlorine atom, which is displaced in a nucleophilic substitution reaction.

These preferred reactive dyes are commonly known as "triazinyl dyes". Examples of this type of dye that are particularly suitable for use in the separation of biological or related substances by the process of the present invention include those sold under the trade marks Cibacron (Ciba Ltd) and Procion (ICI) for example Cibacron Orange G-E, Cibacron Brilliant Blue FBR-P, Cibacron Blue F3G-A, Cibacron Brilliant Red 3B-A, Cibacron Brown 3GR-A, Cibacron Scarlet 2G, Cibacron Scarlet 4G-P, Cibacron Brilliant Red B-A, Procion Brilliant Orange HGRS, Procion Blue HBS, Procion Brilliant Red H7BS, Procion Orange Brown HGS, Procion Scarlet H3GS, Procion Red H3B, Procion Red HE2B, Procion Red P3BN, Procion Red MX2B, Procion Blue MX3G, Procion Yellow MXR, Procion Yellow H5G, Procion Red H8BN, Procion Green H-4G, Procion Brown H-GR, Procion Blue MX-G, Procion Blue HE-RD, Procion Blue H-B, Procion Blue MXR, Procion Yellow HA, Procion Green HE-4BD, Procion Red HE7B, Procion Red MX5B, Procion Red MX8B, Procion Rubine MXB, Procion Scarlet MXG, Procion Orange MXG, Procion Yellow MX6G, Procion Brown H2G, Procion Yellow MX8G, Procion Turquoise HA, Procion Turquoise H7G, Procion Brown MX5BR, Procion Blue MX7RX, Procion Blue MX4GD.

When commercial dyes are used it maybe necessary to remove wetting agents by, for example, washing with an organic solvent, for example, ether or acetone.

In the binding material the ligand is either directly or indirectly attached to a matrix. In the latter case the attachment is through a spacer arm. The matrix may be any support commonly used for affinity chromatography media. Thus polyamino -, polyamido - or polyhydroxylic matrices may be used, especially polysaccharides, such as cellulose, agarose, dextrose and dextran, polyacrylamide, and copolymers of these materials, such as polyacrylamide-agarose gells. (Depending on the conditions employed in the chromatographic process these matrices may be either cross linked or non-cross linked). Alternatively, derivativised metal oxides, such as silica, alumina, titania or zirconia, or glass beads may be used.

Processes for the direct attachment of the ligand precursors of this invention to many of the above matrices are well known to those skilled in the art, see for example U.S. Pat. No. 4,093,612 (Travis and Pannell).

The indirect attachment of the ligand precursors to many of the above matrices is described in our copending U.S. application Ser. No. 372,022 filed concurrently herewith. In the case of indirect attachment the structure of the spacer arm will depend on the choice of matrix and ligand and on the biological or related substance to be separated.

Generally the spacer arm, shown below in its position in the binding material (IV) between the matrix and the ligand, has the structure X—R—Y.

Matrix—X—R—Y—Ligand  (IV)

Its position in a preferred binding material is shown in general formula V

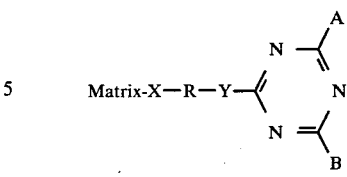

X is an organic or an organometallic functional group, bound directly to the matrix, and having a structure which varies with the choice of matrix. For example, when the matrix is a polysaccharide, particularly cross-linked agarose, X may comprise one or more of the following groups, an alkyl, a substituted alkyl, especially, an alkylalcohol, a diol, a carboxylate, an ether, a thioether, an amido, an amino, an amidino, an imino carboxylate, an isourea, a carbamate or a guanidino group. These groups may be in monomeric, oligomeric or polymeric form. When the matrix is polyacrylamide, X maybe a carboxy group, either alone or attached to an organic group.

When the matrix is silica, X may be

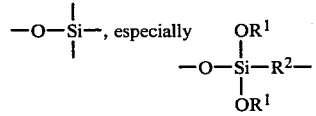

wherein $R^1$ is H or alkyl and $R^2$ is an organic group which may comprise one or more of the following groups, an alkyl, a substituted alkyl, especially an alkylalcohol, a diol, an ether, an amido or an amino group, and optionally one or more of the following groups, an epoxy, a carboxylate, a thioether, an amidino, an imino carboxylate, an isourea, a carbamate or a guanidino group. Again these groups may be in monomeric, oligomeric or polymeric form. Preferably $R^2$ is an optionally substituted alkyl group and/or an alkylether.

Y is a nucleophilic group or atom directly bound to the ligand. In the preferred ligands of the present invention Y is directly bound to the diazinyl or triazinyl ring. Y may be, for example, an alkyl, an ether, a thioether, an amido or an amino group or, which is preferred, it may be —NH—, —O— or —S—.

R is an organic group and may comprise one or more of the following groups an alkyl, an alkene, an α-aminoalkyl, an α-oxyalkyl, an α-thioalkyl, an alkylalcohol, a diol, a carboxylate, an ether, a thioether, an amido, an amino, an amidino, an imino carboxylate, an isourea, a carbamate, a guanidino, a hydrazino, an aromatic or a heterocyclic group. These groups may be in monomeric, oligomeric or polymeric form. Particularly preferred groups include —$CH_2$—$_n$, —NH—$CH_2$—$_n$, —O—$CH_2$—$_n$, or —S—$CH_2$—$_n$ wherein n is from 1 to 12. Other preferred groups include polyethyleneimine, dextran, polyaminoacids, such as polylysine or polyarginine, polyvinylpyrrolidone, polyornithine, polyvinylamine or phenyl derivatives.

The spacer arm may be produced between the matrix and the ligand by any of the following, non-exhaustive list of procedures:

a. Modifying the matrix and reacting the ligand precursor with the modified matrix, b. Modifying the ligand precursor and reacting the modified ligand precursor with the matrix, c. Modifying both the matrix and the ligand precursor and then reacting both modified substances together, or d. Modifying the matrix and then reacting the modified matrix with the unmodified ligand precursor.

Examples of method a. include reacting cross-linked agarose consecutively with cyanogen bromide and an α, w - diaminoalkane to give an aminoalkyl isourea derivative followed by reaction of this modified matrix with a 2, 4 or 6 mono or dichloro triazinyl containing ligand precursor to afford the binding material. Alternatively silica may be reacted consecutively with w - glycidoxyalkyltrialkoxy silane and α, w - aminoalkyl substituted silica and this modified matrix may be reacted with a 2, 4 or 6 - mono or dichlorotriazinyl containing ligand precursor to afford the binding material. In an alternative embodiment the silica may be reacted consecutively with w - thioalkyltrialkoxysilane and a mono or dichlorotriazinyl ligand precursor to afford a sulphur containing binding material. Spacer arms formed by this process include - $OSi(OR^1)_2(CH_2)_3OCH_2CH(OH)CH_2NH(CH_2)_6$ NH— and —$OSi(OH)_2CH_2CH_2CH_2S$—.

Examples of method b. include reacting the mono or dichloro substituted ligand precursor with an α, w - diaminoalkane and then adding this modified ligand to cyanogen bromide activated cross-linked agarose to form the binding material.

Examples of method c. include reacting the mono or dichloro substituted ligand precursor with an α, w - diaminoalkane, separately reacting silica with w - glycidoxyalkyltrialkoxysilane and the adding the modified ligand precursor to the modified matrix to form the binding material. Spacer arms formed by this process include —$OSi(OR^1)_2(CH_2)_3OCH_2CH(OH)CH_2NH(CH_2)_6NH$—.

Examples of method d. include reacting silica with w - glycidoxyalkltrialkoxysilane under acidic conditions to form a diol and then reacting the modified matrix with a 2, 4 or 6 - mono - or dichlorotriazinyl containing ligand precursor. Spacer arms formed by this process include —$OSi(OR^1)_2(CH_2)_3OCH_2CH(OH)CH_2O$—.

The process of the present invention may be performed at atmospheric pressure. Altnernatively the various phases may be performed under pressure, especially under conditions of high pressure. In the latter case, column pressures of between about 100 and 3,500 psi are preferred and the matrix must be compatible with these pressures. (Cross-linked polymers and metal oxides have been shown to meet these requirements.)

The conditions and methods employed in conventional high pressure liquid chromatography (HPLC) and affinity chromatography may be used when the process of the present invention is conducted at high pressure. Generally all three affinity chromatographic phases (contact, washing and eluting) are performed under high pressure, but in one embodiment of the process of the present invention the eluting phase may be performed at atmospheric pressure.

Under these conditions the liquid flow rate through the binding material will depend on the pressure adopted, but is typically between about 0.1 and 3.0 ml/min, preferably 0.5 and 2 ml/min.

Further, at high pressure the binding material is generally retained on a chromatographic column of rigid construction, typically metal construction. The length and width of the column, together with the particle size of the binding material will generally be varied with the quantity of the biological or related substance to be separated. In order to scale up a high pressure procedure from an analytical to a preparative scale and to achieve the same degree of separation in the same time for the same pressure drop, the column length and width together with the particle size of the binding material should be increased.

The nature of the contact, washing and eluting solutions will depend on the nature of the binding material and of the biological or related substance to be separated.

Generally the contact solution comprises the mixture containing the biological or related substance and a salt of the metal ion both dissolved in a buffer solution. Alternatively, in some cases, the contact solution may simply comprise the mixture in a buffer solution. In this latter embodiment, however, before the contact is passed through the chromatographic column, said column must first be treated with a buffer solution containing the metal salt.

The buffer solution will generally be a solution of the salts of weak acids or bases. In particular tris-maleate, tris-HCl or phosphate buffer is preferred. However, in certain cases, a zwitterionic buffer such as N-2-hydroxyethyl piperazine -N'-2-ethane sulphonic acid, sodium salt (HEPES) or 3-(N-morpholino) propanesulphonic acid, sodium salt (MOPS) is preferred.

The preferred pH of the buffer solution will depend on the biological or related substance to be separated. Generally, for enzymes and for other biological or related substances the preferred pH will be between about 5 and 9, most preferable between about 5.5 and 8.

The concentration of the metal ion in the contact solution will also depend on the biological or related substance to be separated. Generally metal ion concentrations of above 0.1 mM, most especially between about 0.2 mM and 10 mM, will be preferred.

The washing solution, which is used to remove non-binding species from the column, will generally be a buffer solution containing a metal salt. The metal salt, buffer solution, pH and metal ion concentration will generally be the same as that used in the contact solution.

The eluting solution may be (i) A buffer solution of the type referred to above containing a chelating agent, especially a nitrogen containing agent such as ethylenediamine, diethylenetriamine, triethylenetetramine, glycine, iminodiacetate, nitrilotriacetate, o-phenanthroline, bipyridyl, pyridine, hydroxynicotinic acid, pyridine dicarboxylic acid or ethylenediamine tetra acetic acid (EDTA), (ii) A simple buffer solution of the type referred to above. If such a buffer solution is used alone and not in conjunction with another eluting solution then its pH will be either above or below the pH of the contact and washing solutions, (iii) A buffer solution of the above type containing an alkali metal, especially a sodium or potassium, salt, (iv) a buffer solution of the above type containing a desorbing agent specific for the adsorbed biological substance. When the biological substance is a protein such a desorbing agent may be an enzyme substrate, cofactor, inhibitor or analogues thereof. Optionally, such a solution may also contain a metal salt comprising a metal ion upon which the biological or related substance depends for its activity, (v) a mixture of two or more of (i) to (iv), or (vi) two or more of (i) to (iv) passed consecutively down the column. In particular, consecutive treatment of the column with solutions (i) and (ii) will, in many cases, be preferred. For example, when the enzyme carboxypeptidase G2 is bound on a Sepharose 6B-Procion Red H8BN column in the presence of $Zn^{2+}$ the enzyme may be eluted by consecutive treatment of the column with 0.01 M EDTA in 0.02 M tris-HCl (pH 5.8) followed by 0.1 M Tris-HCl (pH7.3). Elution of a biological or related substance, particularly an enzyme, under these conditions is particularly useful and advantageous over prior art processes since, after elution, there is no need to remove substrates, substrate analogues or chelating agents from the biological or related substance. This may be a particularly important benefit in the separation of substances which exhibit therapeutic activity.

The invention further comprises any biological or related substance whenever separated from a mixture or purified by the process of the present invention. Such substances will include peptides, polypeptides, proteins, nucleotides, polynucleotides nucleic acids, steroids, lipids and hormones. Generally, however, the biological or related substance will be an enzyme, protein or polypeptide, for example albumin such as ovalbumin, kinases such as hexokinase, glycerokinase or urokinase, carboxypeptidases, alkaline phosphatases, nucleases such as restriction endonucleases, dehydrogenases such as glyceraldehyde - 3 - phosphate dehydrogenase, esterases, DNA or RNA binding proteins.

The process and products of the present invention will now be described by way of example only with particular reference to the FIGURE in which is shown a Carboxypeptidase G2 elution profile demonstrating selective removal of the enzyme from a Sepharose 6B/Procion Red H8BN binding material with pH shock after chelation to the metal ion ($Zn^{2+}$) with EDTA.

MATERIALS

The triazine dyes (trade name: Procion) were kindly donated by Dr. C. V. Stead, ICI Organics Division, Manchester, U.K. Cibacron Blue F3G-A (Procion Blue H-B, Reactive Blue 2, CI 61211) was obtained from Ciba-Geigy Ltd., U.K. Sepharose 6B was from Pharmacia (GB) Ltd., London, U.K. Carboxypeptidase G2 (10 U/mg) was produced by the Microbial Technology Laboratory, PHLS Centre for Applied Microbiology and Research, Porton Down, Nr. Salisbury, U.K. Ovalbumin, hexokinase (ATP: D-hexose 6-phosphotransferase, EC 2.7.1.1: yeast, Type C-300, 375 U/mg) and alkaline phosphatase (orthophosphoric monoester phosphohydrolase (alkaline optimum) EC 3.1.3.1: calf intestinal mucosa, Type I-S, 2 U/mg) were from Sigma (London) Chemical Co., Poole, Dorset, U.K. The chelating agents 2,2'- and 4,4'-bipyridyl were also from Sigma (London) Chemical Co., Poole, Dorset, U.K. Aldrich Chemical Co., the Old Brickyard, New Road, Gillingham, Dorset, U.K., supplied the 6-hydroxynicotinic acid. All other chelating agents and chemicals, which were of Analar grade when available were from BDH Chemicals, Poole, Dorset, U.K., unless otherwise stated.

METHODS

EXAMPLE 1

A. Preparation of Binding Material

Procion Red H8BN (Trade Mark) was washed with acetone and then with ether.

Sepharose 6B (Trade Mark, 10 g) was suspended in water (45 ml) containing pre-washed Procion Red H8BN (100 mg). The suspension was stirred for 5 mins at 15° C. After this time a 5M aqueous solution of sodium chloride (5 ml) was added and the reaction mixture was stirred for a further 30 minutes at 15° C. A 5M aqueous solution of sodium hydroxide (1.2 ml) was then added to the reaction mixture and the stirring was continued at 22° C. for 72 hr. On completion of the reaction the binding material was washed consecutively with water, 6M aqueous solution of urea and water and was then suspended in a 0.1M buffer solution of Tris-HCl (pH 7.3) and, if desired, stored at 4° C.

B. Determination of Bound Dye

Bound dye levels are expressed as mg dye per gm (wet weight) matrix. These levels were determined by hydrolysing the dye/matrix binding material to give a hydroxy triazinyl dye and then determining the amount of hydroxy dye produced by optical density measurements at an absorption maximum of the hydroxy dye.

C. Separation of carboxypeptidase G2 on Sepharose 6B/Procion Red H8BN column in the presence of zinc ions A standard affinity chromatographic column (0.7 cm × 2.6 cm) was packed with 1 g of Sepharose 6B/Procion Red H8BN binding material (prepared as in 1A above). The column was then equilibrated with 0.1M Tris - HCl buffer (pH 7.3).

The contact solution (1 ml), made up of carboxypeptidase G2 (20 mg, 10 iu/mg) and zinc chloride or zinc sulphate (to 0.2 mM) dissolved in 0.1M Tris - HCl (pH 7.3), was then loaded onto the column. Finally a further 10 ml aliquot of the contact solution, but without the enzyme was passed down the column to remove any non-binding enzyme from the column.

The amount of enzyme retained on the column was determined by analysing the solution eluted from the column for carboxypeptidase G2.

The assay for carboxypeptidase G2 was based on a previously published procedure (J. L. McCullough et al, J Biol Chem, 1971, 246, 7207). The reaction mixture contained in a total volume of 1 ml was: methotrexate (4-amino-$N^{10}$-methylpteroylglutamate, Lederle Laboratories), 60 nmol; $ZnCl_2$, 0.2 μmol Tris-HCl, pH 7.3, 100 μmole. The reaction was initiated by the addition of enzyme (0.1–1.0 units) and the change in absorbance at 320 nm and 37° C. due to hydrolysis of methotrexate to 2,4-diamino-$N^{10}$-methylpteroate recorded in a Pye-Unicam SP1800 double beam spectrophotometer. The molar absorption coefficient of methotrexate was taken as 8300 $l.mol^{-1}. cm^{-}$ at 320 nm. 1 unit of enzyme activity is defined as that amount of enzyme which catalyses the hydrolysis of 1 μmol methotrexate per min under the conditions specified above.

The % (by activity) of enzyme bound to Sepharose 6B/Procion Red H8BN under these conditions is given in Table I.

D. Separation of carboxypeptidase G2 on a Sepharose 6B/Procion Red H8BN column in the absence of zincions As a control, the process of 1C above was repeated except that the content and washing solutions did not contain zinc chloride or zinc sulphate. The % (by activity) of enzyme bound to the column is given in Table I.

EXAMPLES 2-16

The process of Example 1A to D was repeated except that Procion Red H8BN was replaced by other Procion H, HE or Cibacron F3G - A dyes as the ligand precursor. (NB Procion Red P3BN is a Procion H series dye). The % (by activity) of enzyme bound to each binding material both in the presence and absence of zinc ions is given in Table I.

TABLE I

| Example | Dye linked to Sepharose 6B | Dye conc$^n$ (mg/g. matrix) | % enzyme bound to column | |
|---|---|---|---|---|
| | | | Control | $Zn^{2+}$ present |
| 1. | Procion Red H8BN | 1.3 | 47 | 100 |
| 2. | Procion Red HE3B | 2.3 | 100 | 100 |
| 3. | Procion Red HE7B | 2.45 | 100 | 100 |
| 4. | Procion Yellow HA | 2.25 | 13 | 10 |
| 5. | Procion Yellow H5G | 1.09 | 13 | 85 |
| 6. | Procion Green HE4BD | 1.91 | 97 | 100 |
| 7. | Procion Brown H2G | 1.24 | 19 | 84 |
| 8. | Procion Brown HGR | 1.16 | 3 | 80 |
| 9. | Procion Blue HB | 2.32 | 39 | 96 |
| 10. | Cibacron Blue F3GA | 2.68 | 71 | 100 |
| 11. | Procion Red H3B | 1.91 | 39 | 96 |
| 12. | Procion Red P3BN | 0.97 | 84 | 96 |
| 13. | Procion Green H4G | 2.2 | 26 | 80 |
| 14. | Procion Torquoise HA | 0.17 | 13 | 11.5 |
| 15. | Procion Torquoise H7G | 0.4 | 13 | 8 |
| 16. | Procion Blue HERD | 3.74 | 93 | 100 |

EXAMPLE 17

A. Preparation of Binding Material

Procion Blue MXR (Trade Mark) was washed with acetone and then with ether.

Sepharose 6B (Trade Mark, 10 g) was suspended in water (45 ml) containing pre-washed Procion Blue MXR (100 mg). The suspension was stirred for 5 mins at 15° C. After this time a 5M aqueous solution of sodium chloride (5 ml) was added and the reaction was stirred for a further 30 mins at 15° C. A 5M aqueous solution of sodium hydroxide (0.12 ml) was then added to the reaction mixture and the stirring was continued for 2 hr at 22° C. On completion of the reaction the binding material was washed consecutively with water, 6M aqueous solution of urea and water and was then suspended in a 0.1M buffer solution of Tris -HCl (pH 7.3) and, if desired, stored at 4° C. B,C,D. The process of Example 1 was repeated except that the binding material prepared by the method of 17A above replaced the binding material prepared by the method of 1A.

The % (by activity) of enzyme bound to the Sepharose 6B/Procion Blue MXR binding material both in the presence and absence of zinc ions is given in Table II.

EXAMPLES 18-32

The process of Example 17A to D was repeated except that Procion Blue MXR was replaced by other Procion MX dyes as the ligand presursor.

The % (by activity) of enzyme bound to each binding material both in the presence and absence of zinc ions is given in Table II.

TABLE II

| Example | Dye linked to Sepharose 6B | Dye conc$^n$ (mg/g. matrix) | % enzyme bound to column | |
|---|---|---|---|---|
| | | | Control | $Zn^{2+}$ present |
| 17. | Procion Blue MXR | 4.9 | 58 | 100 |
| 18. | Procion Red MX2B | 1.9 | 23 | 92 |
| 19. | Procion Red MX5B | 2.3 | 19 | 88 |
| 20. | Procion Red MX8B | 3.9 | 42 | 100 |
| 21. | Procion Rubine MXB | 1.6 | 68 | 96 |
| 22. | Procion Scarlet MXG | 4.7 | 29 | 96 |
| 23. | Procion Orange MXG | 4.0 | 16 | 84 |
| 24. | Procion Yellow MXR | 4.0 | 19 | 96 |
| 25. | Procion Yellow MX6G | 2.3 | 16 | 76 |
| 26. | Procion Yellow MXR | 5.7 | 36 | 100 |
| 27. | Procion Blue MX3G | 2.8 | 19 | 96 |
| 28. | Procion Yellow MX8G | 1.8 | 19 | 80 |
| 29. | Procion Brown MX5BR | 4.3 | 64 | 100 |
| 30. | Procion Blue MX7RX | 3.4 | 19 | 84 |
| 31. | Procion Blue MXG | 2.2 | 93 | 100 |
| 32. | Procion Blue MX4GD | 2.6 | 58 | 96 |

EXAMPLE 33-38

The procedure of Example 1A to D was repeated except that zinc chloride or zinc sulphate was replaced by other metal salts and that prior to equilibration with Tris - HCl buffer, the column was washed with 0.1M EDTA.

The % (by activity) of enzyme bound to Sepharose 6B/Procion Red H8BN in the presence of various metal ions is given in Table III.

TABLE III

| Example | Metal ion | Metal Salt | % Enzyme Bound |
|---|---|---|---|
| Control | — | — | 15 |
| 1 | $Zn^{2+}$ | Chloride | 100 |
| 33 | $Co^{2+}$ | Chloride | 100 |
| 34 | $Cu^{2+}$ | Chloride or Sulphate | 98 |
| 35 | $Ni^{2+}$ | Chloride | 94 |
| 36 | $Al^{3+}$ | $KAl(SO_4)_2$ | 22 |
| 37 | $Ba^{2+}$ | Chloride | 49 |
| 38 | $Ca^{2+}$ | Chloride | 3 |

EXAMPLE 39A

The process of Example 1 was repeated except that the 0.1M Tris - HCl (pH 7.3) buffer was replaced by a 0.1M Tris - HCl (pH 8.5) buffer and the column was prewashed with 0.1M EDTA before equilibration in 0.1M Tris - HCl (pH 8.5).

EXAMPLES 39B AND C

The process of Example 39A was repeated except that the concentration of zinc chloride or zinc sulphate was increased to 0.4 mM and 0.8 mM.

The % (by activity) of enzyme bound to the Sepharose 6B/Procion Red H8BN under the conditions of Examples 39A, B and C is given in Table IV.

EXAMPLES 40-45 A, B and C

The processes of Examples 39A, B and C were repeated except that zinc chloride or zinc sulphate was replaced by other metal salts.

The % (by activity) of enzyme bound to the Sepharose 6B/Procion Red H8BN in the presence of various metal ions is given in Table IV.

TABLE IV

| Example | Metal ion | Metal salt | % Enzyme bound A(0.2 mM) | B(0.4 mM) | C(0.8 mM) |
|---|---|---|---|---|---|
| Control | — | — | 15 | 15 | 15 |
| 39 | $Zn^{2+}$ | Chloride or Sulphate | 100 | 100 | 100 |
| 40 | $Co^{2+}$ | Chloride | 24 | 58 | 92 |
| 41 | $Cu^{2+}$ | Chloride or Sulphate | 15 | 37 | 34 |
| 42 | $Ni^{2+}$ | Chloride | 18 | 41 | 35 |
| 43 | $Ba^{2+}$ | Chloride | 15 | 15 | 14 |
| 44 | $Ca^{2+}$ | Chloride | 13 | 14 | 10 |
| 45 | $Al^{3+}$ | $KAl(SO_4)_2$ | 13 | 14 | 13 |

EXAMPLE 46A

The procedure of Example 1 was repeated except that the dye concentration (mg/g matrix) was increased to 1.7 and the 0.1M Tris - HCl (pH 7.3) buffer was replaced by 0.1M Tris-Maleate (pH 6.0).

EXAMPLE 46B

The procedure of Example 1 was repeated except that the dye concentration (mg/g matrix) was increased to 1.7.

EXAMPLE 46C

The procedure of Example 1 was repeated except that the dye concentration (mg/g matrix) was increased to 1.7 and the 0.1M Tris - HCl (pH 7.3) buffer was replaced by 0.1M Tris-HCl (pH 8.5) buffer.

EXAMPLES 47–48A, B and C

The procedures of Examples 46A, B and C were repeated except that Procion Red H8BN was replaced by Procion Red P3BN and Cibacron Blue F3GA respectively.

The % (by activity) of enzyme bound to the Sepharose 6B/ligand binding material under the conditions of Examples 47–48A, B and C is given in Table V.

EXAMPLE 49A

The procedure of Example 17 was repeated except that the dye concentration (mg/g matrix) was increased to 5.4 and the 0.1M Tris-HCl (pH 7.3) buffer was replaced by 0.1M Tris-Maleate (pH 6.0).

EXAMPLE 49B

The procedure of Example 17 was repeated except that the dye concentration (mg/g. matrix) was increased to 5.4.

EXAMPLE 49C

The procedure of Example 17 was repeated except that the dye concentration (mg/g. matrix) was increased to 5.4 and the 0.1M Tris-HCl (pH 7.3) buffer was replaced by 0.1M Tris-HCl (pH 8.5) buffer.

EXAMPLES 50A, B AND C

The procedure of Examples 49A, B and C was repeated except that Procion MXR was replaced by Procion Blue MX4GD.

The % (by activity) of enzyme bound to the binding material under the conditions of Examples 49–50A, B and C is given in Table V.

TABLE V

| | | | % Enzyme bound | | | | | |
|---|---|---|---|---|---|---|---|---|
| | Dye linked to | Dye conc$^n$ | A(pH 6.0) | | B(pH 7.3) | | C(pH 8.5) | |
| Example | Sepharose 6B | (mg/g matrix) | $Zn^{2+}$ present | Control | $Zn^{2+}$ present | Control | $Zn^{2+}$ present | Control |
| 46 | Procion Red H8BN | 1.7 | 100 | 100 | 100 | 45 | 100 | 13 |
| 47 | Procion Red P3BN | 3.5 | 100 | 100 | 100 | 72 | 100 | 20 |
| 48 | Cibacron Blue F3GA | 4.5 | 100 | 100 | 100 | 73 | 100 | 84 |
| 49 | Procion Blue MXR | 5.4 | 100 | 62 | 96 | 38 | 89 | 21 |
| 50 | Procion Blue MX4GD | 2.8 | 100 | 90 | 100 | 38 | 100 | 52 |

EXAMPLE 51

The procedure of Example 1 was repeated. The column was then washed with an aqueous solution containing 0.01M EDTA and 0.02M Tris - HCl (pH 5.8), and finally the enzyme was eluted by a 0.1M aqueous solution of Tris-HCl (pH 7.3).

The % (by activity) of the total carboxypeptidase G2 eluted from the column in the elution step was determined by the assay procedure outlined in Example 1.

Carboxypeptidase G2 was purified more than thirty-fold and 50–80% of enzyme activity was recovered in 0.2 column volumes. The enzyme was homogeneous (more than 550 iu/mg, by iso-electric focussing and SDS - polyacrylamide gel electrophoresis), c.f the starting material which had an activity of 20 iu/mg.

The results are given in Table VI and the elution profile (of Carboxypeptidase G2) under these conditions is illustrated in the FIGURE.

EXAMPLES 52–54

The procedure of Example 51 was repeated except that zinc chloride or zinc sulphate was replaced by other metal salts.

The results are given in Table VI.

TABLE VI

| | | % Enzyme bound and recovered | | |
|---|---|---|---|---|
| Example | $M^{2+}$ | Contact in 0.1 M Tris-HCl (pH 7.3) plus $M^{2+}$ (0.2 mM) | Wash with 0.01 M EDTA, 0.2 M Tris-HCl (pH 5.8) | Elute with 0.1 M Tris-HCl (pH 7.3) |
| Control | — | 15 | — | — |
| 51 | $Zn^{2+}$ | 100 | — | 88 |
| 52 | $Co^{2+}$ | 100 | — | 82 |
| 53 | $Cu^{2+}$ | 98 | — | 66 |

TABLE VI-continued

| | | % Enzyme bound and recovered | | |
|---|---|---|---|---|
| Example | $M^{2+}$ | Contact in 0.1 M Tris-HCl (pH 7.3) plus $M^{2+}$ (0.2 mM) | Wash with 0.01 M EDTA, 0.2 M Tris-HCl (pH 5.8) | Elute with 0.1 M Tris-HCl (pH 7.3) |
| 54 | $Ni^{2+}$ | 94 | — | 57 |

EXAMPLE 55

The procedure of Example 1 was repeated. The enzyme was eluted from the Sepharose 6B/Procion Red H8BN binding material by passing an aqueous solution (pH 7.3) containing triethylenetetramine (10 mM) and Tris-HCl (0.1M) through the column. The % (by activity) of total Carboxypeptidase G2 recovered from the column was determined by the assay method described in Example 1.

Results are given in Table VII.

EXAMPLES 56–66

The procedure of Example 55 was repeated except that the triethylenetetramine was replaced by other chelating agents. The % (by activity) of total Carboxypeptidase G2 recovered from the column is given in Table VII.

TABLE VII

| Example | Chelating Agent | % Enzyme Recovery | Column Volumes of Elutant required to elute enzyme |
|---|---|---|---|
| 55 | Triethylenetetramine | 95 | 4 |
| 56 | Ethylenediamine | 22 | 14 |
| 57 | Diethylenetriamine | 54 | 16 |
| 58 | Glycine | 8 | 10 |
| 59 | Iminodiacetate | 20 | 14 |
| 60 | Nitrilotriacetate | 60 | 12 |
| 61 | o-Phenanthroline | 0 | — |
| 62 | 4,4-Bipyridyl | 0 | — |
| 63 | 2,2-Bipyridyl | 97 | 4 |
| 64 | Pyridine | 0 | — |
| 65 | 6-Hydroxynicotinic acid | 0 | — |
| 66 | Pyridine-2,6-dicarboxylic acid | 91 | 6 |

EXAMPLE 67

The procedure of Example 1 was repeated except that calf intestine alkaline phosphatase replaced carboxypeptidase G2 as the enzyme, the concentration of zinc chloride or sulphate was increased to 2.0 mM and 0.1M Tris-HCl buffer (pH 7.3) was replaced by 5.0 mM HEPES buffer (pH 7.5).

The amount of enzyme retained on the column was determined by analysing the solution eluted from the column for alkaline phosphatase.

Calf intestinal alkaline phosphatase activity was monitored by following the production of p - nitrophenolate anion from p-nitrophenylphosphate at pH 10.5 and 405 mm (O.A. Bessey et al *J Biol Chem*, 1946, 164, 321). The assay mixture contained in a total volume of 1 ml: glycine-NaOH buffer, pH 10.5, 100 μmol; p-nitrophenylphosphate, 6 μmol; $MgCl_2$, 1 μmol; $ZnCl_2$, 0.1 μmol. The reaction was initiated by the addition of enzyme solution (10 μl, 100 μg, 0.11 units) and the change in absorbance at 405 nm recorded. The molar absorbance coefficient of the p-nitrophenolate anion was 18500 $mol^{-1} cm^{-1}$ at 405 nm. 1 unit enzyme activity is defined as that amount of enzyme which catalyses the formation of 1 μmol p-nitrophenolate anion per min at 37° C.

The % (by activity) of enzyme bound to Sepharose 6B/Procion Red H8BN under these conditions is given in Table VIII.

EXAMPLES 68–71

The procedure of Example 67 was repeated except that other Procion H or HE dyes replaced Procion Red H8BN. Results of % (by activity) enzyme bound to the column are given in Table VIII.

EXAMPLE 72

The procedure of Example 17 was repeated except that calf intestine alkaline phosphatase replaced carboxypeptidase G2 as the enzyme, the concentration of zinc chloride or zinc sulphate was increased to 2.0 mM and 0.1M tris-HCl buffer (pH 7.3) was replaced by 5.0 mM HEPES buffer (pH 7.5).

Further, the enzyme assay procedure of Example 67 was employed. Results are given in Table VIII.

EXAMPLES 73–74

The procedure of Example 72 was repeated except that other Procion MX dyes replaced Procion Blue MXR. Results are given in Table VIII.

TABLE VIII

| Example | Dye linked to Sepharose 6B | Dye conc$^n$ (mg/g matrix) | % Enzyme bound (pH 7.5) +$Zn^{2+}$ | % Enzyme bound (pH 7.5) −$Zn^{2+}$ |
|---|---|---|---|---|
| 67 | Procion Red H8BN | 1.05 | 100 | 80 |
| 68 | Procion Red P3BN | 3.5 | 100 | 89.5 |
| 69 | Procion Green H4BD | — | 100 | 98 |
| 70 | Procion Yellow HA | 1.0 | 80 | 12 |
| 71 | Procion Green H4G | 0.32 | 94 | 87.5 |
| 72 | Procion Blue MXR | 5.4 | 100 | 73 |
| 73 | Procion Blue MX4GD | 2.8 | 100 | 85.5 |
| 74 | Procion Red MX8B | — | 94 | 51.5 |

EXAMPLES 75–78

The procedure of Example 70 was repeated except that the pH of the 5.0 mM HEPES buffer solution was reduced. Results are given in Table IX.

TABLE IX

| Example | pH | % Enzyme bound +$Zn^{2+}$ | % Enzyme bound −$Zn^{2+}$ |
|---|---|---|---|
| 70 | 7.5 | 80 | 12 |
| 75 | 7.2 | 5 | 0 |
| 76 | 7.0 | 4.5 | 0 |
| 77 | 6.8 | 0 | 0 |
| 78 | 6.5 | 0 | 0 |

EXAMPLES 79–83

The procedure of Example 70 was repeated except that zinc chloride or zinc sulphate was replaced by other metal salts. Results are given in Table X.

TABLE X

| Example | Metal Ion | Salt | % Enzyme bound |
|---|---|---|---|
| Control | — | — | 12 |
| 70 | $Zn^{2+}$ | Chloride or Sulphate | 80 |
| 79 | $Co^{2+}$ | Chloride | 12 |
| 80 | $Ni^{2+}$ | Chloride | 18 |
| 81 | $Ba^{2+}$ | Chloride | 4 |
| 82 | $Ca^{2+}$ | Chloride | 4 |

TABLE X-continued

| Example | Metal Ion | Salt | % Enzyme bound |
|---------|-----------|------|----------------|
| 83 | $Al^{3+}$ | $KAl(SO_4)_2$ | 27 |

EXAMPLES 84–86

The procedure of Example 70 was repeated except that the concentration of zinc chloride or zinc sulphate was varied. Results are given in Table XI.

TABLE XI

| Example | $Zn^{2+}$ conc$^n$ (mM) | % Enzyme bound |
|---------|-------------------------|----------------|
| Control | 0 | 12 |
| 84 | 1 | 25 |
| 70 | 2 | 80 |
| 85 | 3 | 96 |
| 86 | 4 | 100 |

EXAMPLE 87

The procedure of Example 1 was repeated except that carboxypeptidase G2 was replaced by yeast hexokinase as the enzyme the concentration of zinc chloride or zinc sulphate was either 10 mM or 1 mM, 0.1M Tris - HCl buffer (pH 7.3) was replaced by 30 mM Tris-HCl buffer (pH 7.5) and Procion Red H8BN was replaced by Cibacron Blue F3GA as the ligand.

The amount of enzyme retained on the column was determined by analysing the solution eluted from the column for Yeast Hexokinase.

Yeast Hexokinase activity was followed in a coupled reaction P. B. Garland et al, Nature (London), 1962, 196, 987. The assay mixture contained in a total volume of 1 ml: triethanolamine-HCl buffer, pH 7.6, 100 μmol; ATP 2 μmol; NADH, 0.3 μmol; KCl, 2 μmol; $MgCl_2$, 6 μmol; phosphoenolpyruvate, 12 μmol; lactate dehydrogenase/pyruvate kinase, 40 μg and yeast hexokinase, 100 μg, 1.5 units. The reaction was initiated by the addition of D-glucose (2.5 μmol) and the change in absorbance at 340 nm recorded. 1 unit enzyme activity is defined as that amount of enzyme which catalyses the conversion of 1 μmol. NADH per min at 37° C. The molar absorption coefficient of NADH was taken as 62201. $mol^{-1}cm^{-1}$ at 340 nm.

The % (by activity) of enzyme bound to Sepharose 6B/Cibacron Blue F-3GA under these conditions is given in Table XII.

Examples 88–93

The procedure of Example 87 was repeated except that a 30 mM Tris-HCl (pH 7.2) buffer was used and various metal salts (10 mM or 1 mM) replaced zinc chloride or zinc sulphate. Results are given in Table XII.

TABLE XII

| Example | Metal Ion | Salt | % Enzyme-bound (10 mM) | % Enzyme bound (1 mM) |
|---------|-----------|------|------------------------|-----------------------|
| Control | — | — | 20.5 | 20.5 |
| 87 | $Zn^{2+}$ | Chloride or Sulphate | 100 | 100 |
| 88 | $Co^{2+}$ | Chloride | 100 | 87 |
| 89 | $Cu^{2+}$ | Chloride or Sulphate | 100 | 90 |
| 90 | $Ni^{2+}$ | Chloride | 100 | 100 |
| 91 | $Ba^{2+}$ | Chloride | 72 | 23 |
| 92 | $Ca^{2+}$ | Chloride | 100 | 64 |

TABLE XII-continued

| Example | Metal Ion | Salt | % Enzyme-bound (10 mM) | % Enzyme bound (1 mM) |
|---------|-----------|------|------------------------|-----------------------|
| 93 | $Al^{3+}$ | $KAl(SO_4)_2$ | 35 | 23 |

Example 94

The procedure of Example 1 was repeated except that ovalbumin replaced carboxypeptidase G2 potassium aluminium sulphate (2 mM) replaced zinc chloride or sulphate as the metal salt and 0.1 M Tris-HCl buffer (pH 7.3) was replaced by 0.03 M Tris-HCl buffer (pH 7.2).

The amount of protein retained on the column was determined by analysing the solution eluted from the column for ovalbumin.

Ovalbumin was determined by absorbance at 280 nm, D Warburg et al., Biochem Z., 1931, 242, 207.

The % (by activity) of enzyme bound to Sepharose 6B/Procion Red H8BN under these conditions is given in Table XIII.

Examples 95–97

The procedure of Example 94 was repeated except that other Procion H or HE dyes replaced Procion Red H8BN. Results of % (by activity) enzyme bound to the column are given in Table XIII.

Example 98

The procedure of Example 17 was repeated except that ovalbumin replaced carboxypeptidase G2, potassium aluminium sulphate (2 mM) replaced zinc chloride or zinc sulphate as the metal salt and 0.1 M Tris-HCl buffer (pH 7.3) was replaced by 0.03 M Tris-HCl buffer (pH 7.2).

Further the protein was determined as in Example 94. Results are given in Table XIII.

Examples 99–100

The procedure of Example 98 was repeated except that other Procion MX dyes replaced Procion MXR. Results are given in Table XIII.

TABLE XIII

| Example | Dye linked to Sepharose 6B | Dye conc$^n$ (mg/g matrix) | % Protein bound (pH 7.2) $+Al^{3+}$ | % Protein bound (pH 7.2) $-Al^{3+}$ |
|---------|----------------------------|------------------------------|-------------------------------------|-------------------------------------|
| 94 | Procion Red H8BN | 1.59 | 16 | 0 |
| 95 | Procion Yellow HA | 1.72 | 18 | 6 |
| 96 | Cibacron Blue F3GA | 4.47 | 97 | 3 |
| 97 | Procion Green H4G | 0.21 | 16 | 0 |
| 98 | Procion Blue MXR | 8.49 | 20 | 3 |
| 99 | Procion Red P3BN | 4.60 | 14 | 3 |
| 100 | Procion Orange MXG | 9.37 | 58 | 0 |

Example 101–103

The procedure of Example 1 was repeated except that the concentration of zinc chloride or zinc sulphate was varied. The % (by activity) of enzyme bound to the column is given in Table XIV.

TABLE XIV

| Example | $Zn^{2+}$ conc$^n$ (mM) | % Enzyme Bound |
|---------|-------------------------|----------------|
| 101 | 0.025 | 50 |
| 102 | 0.05 | 80 |
| 103 | 0.1 | 100 |

TABLE XIV-continued

| Example | $Zn^{2+}$ conc$^n$ (mM) | % Enzyme Bound |
|---------|-------------------------|----------------|
| 1       | 0.2                     | 100            |

Examples 104–107

The binding of tyrosinase (EC 1.14.18.1, a copper containing enzyme) to Sepharose 6B - Procion Blue HERD was examined in the presence of various metal ions. The buffer system employed was 0.03 M Tris HCl (pH 7.4). Results of % (by activity) enzyme bound are given in Table XV.

TABLE XV

| Example | Metal ion | Metal ion concentration (mM) | | | | |
|---------|-----------|---|---|---|---|---|
|         |           | 0 | 1 | 2 | 3 | 4 |
| 104     | $Zn^{2+}$ | 30 | 43 | 77 | 94 | 100 |
| 105     | $Co^{2+}$ | 31 | 30 | 38 | 50 | 61  |
| 106     | $Ni^{2+}$ | 30 | 38 | 69 | 85 | 92  |
| 107     | $Cu^{2+}$ | 33 | 30 | 30 | 22 | 22  |

Example 108 (High Pressure Liquid Affinity Chromatography HPLAC)

The following binding materials were prepared by methods described in our copending U.K. patent application No. 8112897 (Agents Ref: JX/5963/02)

A. Preparation of Binding Material (i) Silica gel (Li-chrosorb Si-60 (Trade Mark), 5 μm, E Merck, 5 g) was suspended in 200 ml of an aqueous solution of glycidoxypropyltrimethoxysilane (1%, pH 5.5; silane Z-6040, Dow Corning). The slurry was treated under reduced pressure in an ultrasonic bath and then heated to and maintained at 90° C. for 2 hr. with occasional shaking. The resulting epoxysilica gel was washed thoroughly with water, dried and could be stored dry without loss of epoxy groups.

(ii) Crude Procion Yellow HA (1 mM) was dissolved in 20 ml H$_2$O. 10 ml of 1,6—diamino hexane (1 M, pH 10.0) was added and the solution was heated at 50° C. for 1 hr. The solution was then added dropwise to 200 ml, 0.3 M HCl and incubated for 5 min at 20° C. The precipitate formed was then removed by centrifugation or filtration and thoroughly washed with 0.3 M HCl. The precipitate was then washed with acetone until the supernatant fraction remained colourless and then dried in air to a yellow powder. The resulting product 6 - aminohexyl - Procion Yellow HA was more than 90% pure, as measured by tlc on silica (2-butanol: 1- propanol: ethyl acetate: water; 20: 40: 10: 30 (v/v/v/v)) and was positive to the 2, 4, 6-trinitrobenzene sulphonic acid test for primary amines.

(iii) To 2 g epoxy - silica (step (i) above) was added 10 ml 0.1 M NaHCO$_3$ - Na$_2$ CO$_3$ (pH 8.6) and 180 mg 6-aminohexyl - Procion Yellow HA (step (ii) above), the slurry was sonicated for 10 min under reduced pressure and then incubated overnight at 30° C. with gentle agitation. The Procion Yellow HA - aminohexyl - epoxysilica binding material was washed with water (250 ml), 50% (v/v) aqueous methanol (200 ml), methanol (200 ml) and either (100 ml) prior to drying in air to a yellow powder.

B. Chromatographic procedure (i) The binding material (1.2 g) was packed in polished '315' stainless steel columns (100 mm × 5 mm; ID, total volume 2.0 ml) using the upward slurry packing technique of P.A. Bristow et al., J Chromatogr., 1977, 131, 57. All chromatographic procedures were performed at ambient temperature (20°–22° C.). The pumping system comprised an Altex Model 110A solvent metering pump (Altex, California, USA) equipped with a pulse dampener. Ultraviolet detection was performed with a variable wavelength detector, 190–700 nm (LC-55, Perkin Elmer) and sample injections were made with a valve injection (Valco, Houston). Enzymes eluted from the High Pressure Liquid Affinity Chromatography (HPLAC) column were detected with an on-line detector system (S.H. Chang et al., J Chromatogr., 1976, 125, 103) comprising a reagent pump (Altex Model 110A), post column reactor, equilibrated to 40° C. in a water bath, and a UV/visible monitor (LC-55, Perkin Elmer). The post column reactor comprised a polished stainless '316'column (100 mm × 5 mm; I.D., total volume, 2.0 ml) containing non-porous glass beads (150 μm) silanised as described by M Glad et al., J Chromatogr., 1980, 200, 254 with the resulting epoxy groups hydrolysed to diols by heating in 10 mm HCl at 75° C. for 30 min.

(ii) The binding material was packed into 100 mm × 55 mm stainless steel columns by the downward slurry packing technique using a Magnus Scientific Slurry packing unit. 1.5 gm of binding material was suspended in 25 ml methanol and packed into the column at a pressure of 2000 psi. The packing pressure was slowly increased to 3000 psi and this pressure was maintained until 150 ml of solvent had been collected. The solvent was then changed to double distilled water (degassed and filtered through a 0.45 μMillipore filter) and a further 150 ml of solvent was collected. The packed column was detached from the apparatus and a staniless steel sinter was fitted to each end.

When not in use the columns were sealed at both ends with plastic plugs and stored at 15° C.

C. Separation of Carboxypeptidase G2

The column was packed with Procion Yellow HA - aminohexyl - epoxysilica binding material by the method described above (108B). It was then equilibrated, at a sample pump pressure of 1200 psi - reagent pump pressure of 200 psi and a flow rate of 1 ml/min, with 10 mH HEPES buffer (pH 7.5). The contact solution (0.1 ml), made up of carboxypeptidase G2 (0.2 mg/ml), 10 iu/mg) and zinc chloride (0.2 mM) dissolved in 0.1 M Tris-HCl buffer (pH 7.5), was then loaded onto the column under pressure (sample pump 1200 psi, reagent pump 200 psi). A further 1 ml aliquot of the contact solution, but without the enzyme, was then passed down the column, under the same pressure, to remove any non-binding species from the column. Using the assay procedure described in Example 1 the % (by activity) of carboxypeptidase G2 that was retained on the column was determined. This was found to be 100% of enzyme activity.

Finally the enzyme was recovered from the column by applying a pulse (0.2 ml) of 0.2 M KCl,

Example 109

A. A Procion Yellow HA - aminohexyl-epoxysilica binding material was prepared as in Example 108A.

B. Separation of Calf Intestine Alkaline Phosphatase (i) The HPLAC procedure of Example 108 was repeated except that alkaline phosphatase replaced carboxypeptidase G as the enzyme.

Using the assay procedure described in Example 67 the % (by activity) of alkaline phosphates that was retained on the column was determined. This was found to be 0%.

(ii) The HPLAC procedure of Example 108 was repeated except that, before the contact solution was loaded onto the column, the binding material was treated with a 0.2 mM solution of zinc chloride. Under these conditions 100% (by activity) of enzyme activity was retained on the column.

Finally the enzyme was recovered from the column by applying a pulse (0.2 ml) of 0.2 M KCL

What we claim is:

1. A process for the affinity chromatographic separation of at least one biological substance from a mixture containing same comprising the steps of:
   a. contacting a contact solution, comprising the mixture containing the at least one biological substance, with a binding material, having a matrix bound either directly or through a spacer arm to a ligand containing at least one group selected from the group consisting of anthraquinone, phthalocyanine and aromatic azo, to bind the at least one biological substance to the binding material;
   b. passing a washing solution through the binding material to remove non-binding species therefrom; and
   c. passing an eluting solution through the binding material to recover the at least one biological substance therefrom, wherein the improvement comprises binding the at least one biological substance to the binding material in the presence of at least one metal ion selected from the group consisting of $Ca^{2+}$, $Sr^{2+}$, $Ba^{2+}$, $Al^{3+}$, $Co^{2+}$, $Ni^{2+}$, $Cu^{2+}$ and $Zn^{2+}$.

2. A process according to claim 1 wherein the at least one metal ion is selected from the group consisting of $Co^{2+}$, $Ni^{2+}$ and $Zn^{2+}$.

3. A process according to claim 2 wherein the at least one metal ion is $Zn^{2+}$.

4. A process according to claim 1 wherein the contact solution comprises the mixture containing the at least one biological substance and the at least one metal ion.

5. A process according to claim 1 comprising binding at least 70% (by activity) of the at least one biological substance to the binding material.

6. A process according to claim 1 wherein the ligand is derived from a reactive dye of general formula III

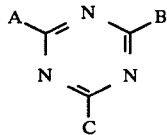

wherein A is an organic substituent containing at least one group selected from the group consisting of anthraquinone, aromatic azo and phthalocyanine, B is selected from the group consisting of an organic substituent, a halogen atom and an optionally substituted amino group and C is a leaving group which is displaced in a nucleophilic substitution reaction.

7. A process according to claim 6 wherein A is a sulphonated anthraquinone group.

8. A process according to claim 6 wherein B is a sulphonated aromatic group.

9. A process according to claim 6 wherein B is a chlorine atom.

10. A process according to claim 6 wherein C is a chlorine atom.

11. A process according to claim 1 wherein the ligand is derived from a reactive dye which is a pyrazinyl, pyrimidinyl, pyridazinyl or sulphone derivative of an anthraquinone or an aromatic azo group.

12. A process according to claim 1 wherein the matrix is selected from the group consisting of a polyamino-, a polyamido- and a polyhydroxylic support.

13. A process according to claim 12 wherein the matrix is selected from the group consisting of a polysaccharide, a polyacrylamide and a copolymer of these polymers.

14. A process according to claim 13 wherein the matrix is selected from the group consisting of cellulose, agarose, dextrose, dextran and polyacrylamide-agarose.

15. A process according to claim 14 wherein the matrix is cross linked.

16. A process according to claim 15 wherein the matrix is attached to the ligand via a spacer arm.

17. A process according to claim 16 wherein the separation is conducted on a high pressure liquid chromatography column at a pressure of between 100 and 3500 psi.

18. A process according to claim 1 wherein the matrix is a metal oxide support.

19. A process according to claim 18 wherein the matrix is selected from the group consisting of silica, alumina, titania, zirconia and glass beads.

20. A process according to claim 19 wherein the matrix is attached to the ligand via a spacer arm.

21. A process according to claim 20 wherein the spacer arm has the structure —Y—R—Y— wherein X is an organic or an organometallic functional group, R is an organic group and Y is a nucleophilic group or atom.

22. A process according to claim 21 wherein R is at least one group selected from the group consisting of alkyl, alkene, αc-aminoalkyl, αc-oxyalkyl, αc-thioalkyl, alkyl alcohol, diol, carboxylate, ether, thioether, amido, amino, amidino, imino carboxylate, isourea, carbamate, guanidino, hydrazino, aromatic and heterocyclic groups and Y is selected from the group consisting of alkyl, ether, thioether, amido, amino, —NH—, —O— and —S—.

23. A process according to claim 22 wherein the binding material has the general formula IV Matrix—X—R—Y—Ligand    IV wherein the matrix is silica, X is

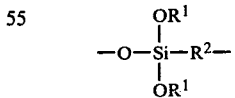

wherein $R^1$ is selected from the group consisting of H and alkyl and $R^2$ is at least one group selected from the group consisting of alkyl, substituted alkyl, diol, ether, amido and amino, R is at least one group selected from the group consisting of alkyl, alkene, αc-aminoalkyl, αc-oxyalkyl, αc-thioalkyl, alkyl alcohol, diol, carboxylate, ether, thioether, amido, amino, amino, amidino, imino carboxylate, isourea, carbamate guanidino, hydrazino, aromatic and heterocyclic groups and Y is selected from the group consisting of alkyl, ether, thioether, amido, amino, —NH—, —O— and —S—.

24. A process according to claim 23 wherein $R^2$ is at least one group selected from the group consisting of alkyl, substituted alkyl and alkyl ether, R is selected from the group consisting of —CH$_2$—$_n$, —NH(CH$_2$—$_n$, —O(CH$_2$—$_n$ and —S(CH$_2$—$_n$ wherein n is from 1 to 12 and Y is selected from the group consisting of —NH—, —O— and —S—.

25. A process according to claim 24 wherein the spacer arm (X—R—Y) is selected from the group consisting of —OSi(OR$^1$)$_2$(CH$_2$)$_3$OCH$_2$CH(OH)CH$_2$NH(CH$_2$)$_6$NH—

—OSi(OR$^1$)$_2$CH$_2$CH$_2$CH$_2$S— and

—OSi(OR$^1$)$_2$(CH$_2$)$_3$OCH$_2$CH(OH)CH$_2$O—.

26. A process according to claim 20 wherein the separation is conducted on a high pressure liquid chromatography column at a pressure of between 100 and 3500 psi.

27. A process according to claim 1 wherein the at least one biological substance is eluted from the binding material by consecutively passing through the binding material a buffer solution, selected from the group consisting of tris-maleate, tris-HCl phosphate, HEPES and MOPS, containing a chelating agent, followed by a buffer solution selected from the group consisting of trismaleate, tris-HCl, phosphate, HEPES and MOPS.

28. A process according to claim 27 wherein the chelating agent is a nitrogen containing chelating agent.

29. A process according to claim 28 wherein the chelating agent is selected from the group consisting of ethylenediamine diethylenetriamine, triethylenetetramine, glycine, iminodiacetate, nitrilotriacetate, 0-phenanthroline, bipyridyl, pyridine, hydroxynicotinic acid, pyridine dicarboxylic acid and EDTA.

30. A process according to claim 1 wherein the at least one biological substance is selected from the group consisting of an enzyme, a polypeptide and a protein.

31. A process according to claim 30 wherein the at least one biological substance is selected from the group consisting of an albumin, a kinase, a carboxypeptidase, an alkaline phosphatase, a nuclease, a dehydrogenase, an esterase, a DNA binding protein and an RNA binding protein.

32. A process according to claim 1 wherein the metal ion is selected from the group consisting of $Al^{3+}$, $Co^{2+}$, $Ni^{2+}$, $Cu^{2+}$, and $Zn^{2+}$.

* * * * *